United States Patent [19]

Gallian et al.

[11] Patent Number: 5,047,246

[45] Date of Patent: Sep. 10, 1991

[54] DIRECT COMPRESSION CYCLOPHOSPHAMIDE TABLET

[75] Inventors: Claude E. Gallian, Newburgh; Charles Williams, Evansville, both of Ind.

[73] Assignee: Bristol-Myers Company, New York, N.Y.

[21] Appl. No.: 242,849

[22] Filed: Sep. 9, 1988

[51] Int. Cl.⁵ .............................................. A61K 9/30
[52] U.S. Cl. .................................. 424/464; 424/465; 424/470; 424/475; 424/479; 424/499
[58] Field of Search ............... 424/489, 464, 465, 470, 424/475, 479, 499

[56] References Cited

U.S. PATENT DOCUMENTS

| | | | |
|---|---|---|---|
| 3,584,114 | 6/1971 | Cavalli et al. | 424/38 |
| 3,725,556 | 4/1973 | Hanssen et al. | 424/357 |
| 3,873,694 | 3/1975 | Kanig | 424/127 |
| 4,072,535 | 1/1978 | Short et al. | 106/210 |
| 4,198,507 | 4/1980 | Barry et al. | 514/869 X |
| 4,218,471 | 8/1980 | Brock et al. | 514/578 |
| 4,439,453 | 3/1984 | Vogel | 106/210 |
| 4,457,907 | 7/1984 | Porter | 424/7.1 |
| 4,753,789 | 6/1988 | Tyers et al. | 514/917 X |
| 4,910,218 | 3/1990 | Bair | 514/443 |

Primary Examiner—Thurman K. Page
Attorney, Agent, or Firm—Robert H. Uloth

[57] ABSTRACT

A directly compressible pharmaceutical composition comprising cyclophosphamide and a partially or fully pregelatinized starch is disclosed. The pharmaceutical composition, when directly compressed into a tablet, exhibits unexpected stability when compared to cyclophosphamide in combination with other direct compression vehicles.

14 Claims, 1 Drawing Sheet

DIRECT COMPRESSION CYCLOPHOSPHAMIDE TABLET

FIELD OF THE INVENTION

This invention relates to a novel pharmaceutical composition. More particularly, this invention relates to an unexpectedly stable pharmaceutical composition comprising cyclophosphamide and a partially or fully pregelatinized starch, which composition can be directly compressed to form a pharmaceutical tablet.

BACKGROUND OF THE INVENTION

The compressed tablet is one of the oldest and most popular unit dosage forms for medicinal substances. The tablet as a dosage form can be traced to well over 1,000 years ago when a procedure for molding solid forms containing medicinal ingredients was recorded. As a result of the introduction of new carriers and compression vehicles, tablets are replacing many forms of pills, powders and capsules. Accordingly, tablets presently represent the largest production volume of all pharmaceuticals.

The reasons for the widespread use of tablets are apparent, since tablets facilitate: (1) administration of medication in an accurate dose; (2) fast and accurate dispensing with less chance of error and contamination: (3) ease of administration: (4) administration in a form in which the time and area of contact between the active ingredient and the taste buds are reduced, thus obviating the physiological problems associated with the oral administration of drugs that possess a bitter taste and, in the case of coated tablets, with drugs that possess a disagreeable odor; (5) release of drugs at specific locations in the gastro-intestinal tract to prevent degradation of drugs sensitive to the low pH environment in the stomach, prevent release of drugs that irritate the gastric mucosa in the stomach, and facilitate local action or preferential absorption at specific sites in the tract: (6) enhanced stability by effecting a marked reduction in the surface of the drug exposed to the environment; (7) rapid production; and (8) economy and ease in storage, packaging and shipping.

There are currently three basic methods for tableting. They are the wet granulation method, the dry granulation method and the direct compression (DC) method. The direct compression method is by far the desired method from the standpoint of processing time and requirements of equipment and materials. However, only a very limited number of pharmaceutical substances possess enough cohesive strength and flowability to allow direct compression without previous granulation. Certain crystalline materials, such as potassium bromide and potassium chloride can be compressed without preliminary treatment. Also, drugs such as aspirin and phenolphthaline can be directly compressed after blending with suitable tableting excipients.

It has been estimated that about 20 percent of the materials used for tableting in the pharmaceutical field may be compressed directly. In order to use this method to a greater extent, many more materials are modified either by treating the material in some special way during early stages of preparation, or by adding a direct compression vehicle, i.e., a dry binder or excipient material which will mix with the active ingredient to provide a flowable powder and form an easily compressible carrier. Exemplary United States patents relating to directly compressible tablets include U.S. Pat. No. 3,584,114 to Cavalli, et al., U.S. Pat. No. 3,725,556 to Hanssen, et al., U.S. Pat. No. 3,873,694 to Kanig, U.S. Pat. No. 4,072,535 to Short, and U.S. Pat. No. 4,439,453 to Vogel.

There are currently several available binders or excipients which can be used as direct compression vehicles. They include spray-dried lactose; anhydrous lactose: microcrystalline cellulose; dicalcium phosphate dihydrate, unmilled; spray-congealed mannitol; ungelatinized starch (e.g., corn starch), and partially or fully pregelatinized starch.

Starch, as defined by the *National Formulary XVI*, "consists of the granules separated from the mature grain of corn {*Zea mays Linne* (Fam.Gramineae)} or of wheat {*Triticum asetivum Linne* (Fam.Gramineae)}, or from tubers of the potato {*Solanum tuberosum Linne* (Fam.Solanaceae)}." Pregelatinized starch is defined by the *National Formulary XVI* as "starch that has been chemically and/or mechanically processed to rupture all or part of the granules in the presence of water and subsequently dried. Some types of pregelatinized starch may be modified to render them compressible and flowable in character." Many types of partially or fully pregelatinized starches are commercially available for use in direct compression tablet formulations.

With the advent of the above described direct compression vehicles, drug manufacturers are seeking to formulate or reformulate pharmaceutically active compounds into compositions which are directly compressible into tablets. One such compound is cyclophosphamide, an anti-neoplastic agent manufactured by Bristol-Myers Company under the trademark CYTOXAN®, which is currently tableted with specially prepared directly compressible diluent. This DC diluent is produced by a wet granulation process. However, processing cyclophosphamide using wet granulation method has certain drawbacks. A major problem is that it is difficult to control the moisture of the resulting tablet. A second problem is that the dissolution rate, i.e., the rate at which the tablet dissolves in water, decreases over time. The third problem is that the dissolution rate of the tablet varies from batch to batch, with some batches having unacceptably low rates.

Obviously, a direct compression cyclophosphamide tablet would be desirable. Unfortunately, cyclophosphamide is not one of the few known compounds which possesses the cohesive strength and flowability to allow direct compression. Thus, there is a need for a directly compressible composition comprising cyclophosphamide and a direct compression vehicle, which composition obviates the problems resultant from wet processing.

Accordingly, it is an object of this invention to provide a directly compressible pharmaceutical composition comprising cyclophosphamide and a direction compression vehicle.

SUMMARY OF THE INVENTION

Surprisingly, a directly compressible pharmaceutical composition has been discovered comprising cyclophosphamide and a partially or fully pregelatinized starch. It has been found that this composition, when directly compressed into a tablet, exhibits unexpected and remarkable stability when compared to CYTOXAN® tablets or cyclophosphamide in combination with other directly compressible vehicles.

DETAILED DESCRIPTION OF THE INVENTION

Figure 1:
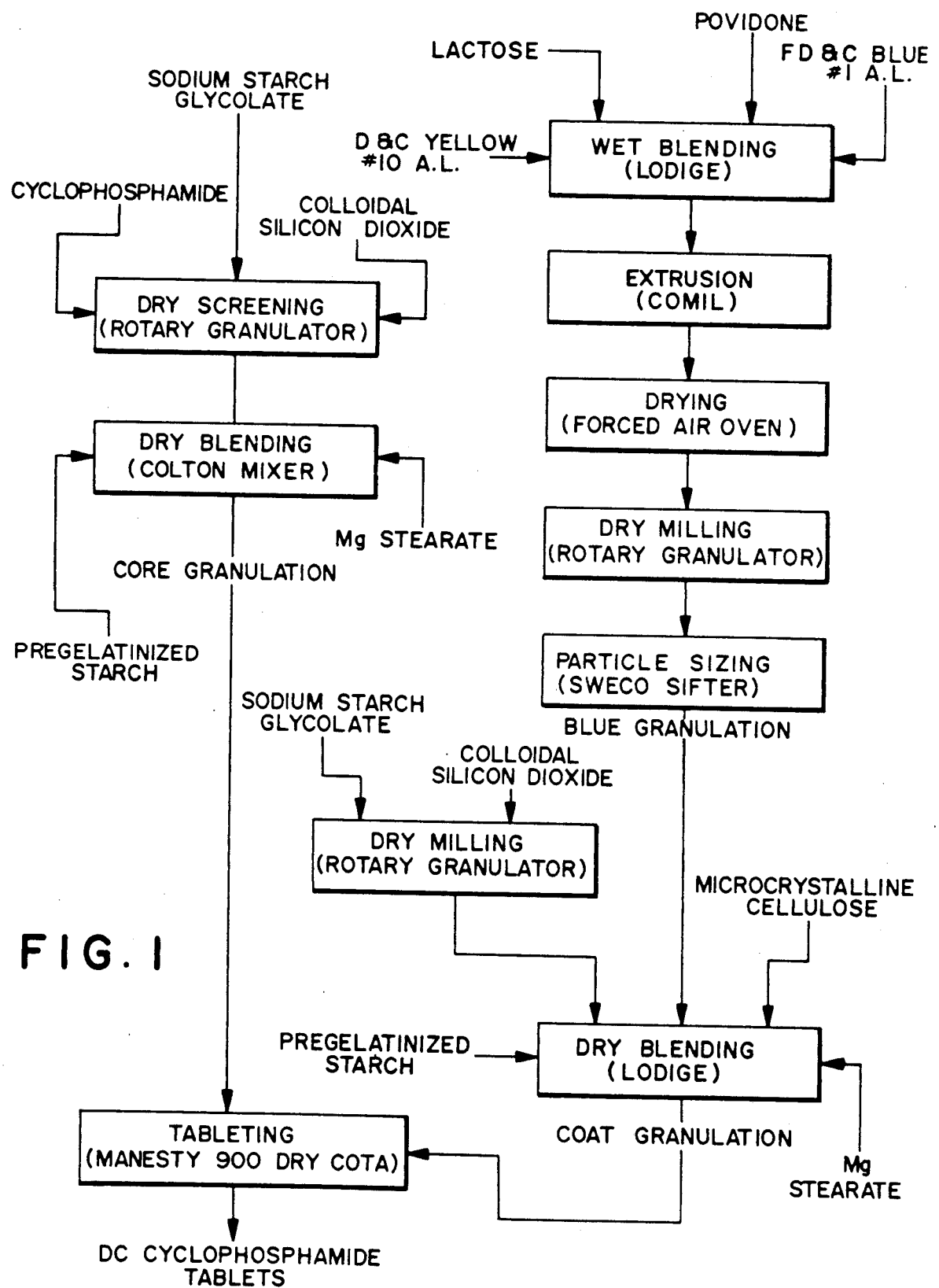
FIG. 1 is a schematic diagram of a process for making a direct compression cyclophosphamide tablet in accordance with this invention.

Cyclophosphamide is listed as a cytotoxic agent by the Environmental Protection Agency. Accordingly, a "core tablet blend" containing the cyclophosphamide is first prepared and compressed to form a compressed core tablet. The compressed core tablet is then covered or encapsulated by a second compressed coating called a "press coat blend", which contains no active ingredients. Thus, persons handling the tablets do not directly contact the carcinogenic cyclophosphamide.

I. THE CORE TABLET BLEND

The core tablet blend in accordance with this invention comprises a mixture of cyclophosphamide, a partially or fully pregelatinized starch, and optionally, additional diluents or other ingredients such as disintegrants, lubricants, glidants, etc.

A. The Cyclophosphamide and Pregelatinized Starch

The cyclophosphamide used in this invention is the crystalline monohydrate form. For purposes of the procedures described below it is preferred that the particle size be approximately 40 mesh or smaller. Due to its low melting point (46° C.), cyclophosphamide is not conducive to milling. When orally administered, cyclophosphamide is usually prescribed in dosages of 25 mg, 50 mg, or 100 mg.

Several different types of partially or fully pregelatinized starch (hereinafter simply "pregelatinized starch") can be used in accordance with this invention. The pregelatinized starch should meet all National Formulary XVI standards and be capable of mixing with cyclophosphamide to form a directly compressible tablet. These skilled in the art can by simple routine experimentation determine those starches capable of forming direct compression tablets with cyclophosphamide, and the optimum mixtures for doing so.

Commercially available pregelatinized starches which can be used include STARCH 1500 (formerly STA-RX 1500), which is a modified, partially gelatinized corn starch produced by Colorcon, Inc., West Point, Penna.; several pregelatinized starches produced by the Hubinger Company, Keokuk, Iowa, including CERI-GEL 300, a five percent modified, fully pregelatinized corn starch, CERI-GEL 433, which is a modified, fully pregelatinized corn starch, PREGEL, which is an unmodified, fully pregelatinized corn starch, INSTANT KEOGEL, which is a 100 percent modified, fully pregelatinized corn starch, and TENDER JEL, which is a 100 percent modified, fully pregelatinized corn starch; WHEATGEL 100, which is a fully pregelatinized wheat starch produced by International Grain Products, Montreal, Canada; and several pregelatinized starches produced by the A. E. Staley Manufacturing Company, Hulton, Ma., including BINASOL 15, which is a modified, fully pregelatinized tapioca starch, BINASOL 81, which is a modified, fully pregelatinized tapioca starch, INSTANT TENDER JEL, which is a 99 percent modified, fully pregelatinized waxy corn starch, and STA-RX, which is a modified, fully pregelatinized corn starch.

It has been found that STARCH 1500 provides the best results, but that the other pregelatinized starches mentioned above will also provide good results. STARCH 1500 is a modified, partially pregelatinized corn starch containing approximately 5 percent amylose, 15 percent amylopectin, and 80 percent unmodified corn starch. STARCH 1500 has a cold water soluble fraction of 10-20 percent.

All starches contain two types of carbohydrate chains, i.e., amylose and amylopectin, which both have the same basic chemical structure. However, they are slightly different, which accounts for their very different individual properties. Amylose has a straight chain molecular make-up, while the amylopectin has a multi-branched make-up. In unmodified corn starch, amylose and amylopectin are randomly mixed throughout the starch grains and are held together by hydrogen bonding that prevents them from functioning independently. The gelatinized process breaks that hydrogen bonding and allows the two chains to function separately.

STARCH 1500, when used as a capsule excipient for aspirin, is known to provide better stability than either anhydrous lactose or microcrystalline cellulose excipients. It is also known that aspirin is an ester that easily undergoes hydrolysis in the solid state when exposed to ambient moisture. STARCH 1500 has a high moisture content; however, this moisture is apparently not available to hydrolyze the aspirin molecule. In contrast, degradation of cyclophosphamide (CY) monohydrate in solid dose forms is initiated by dehydration resulting in the loss of CY monohydrate crystalline structure. CY monohydrate degrades rapidly when the moisture content is less than the monohydrate equivalent. Without being bound by theory, the improved stability is believed to be due to the moisture of STARCH 1500 maintaining the CY in its monohydrate state. This is surprising and unexpected since the moisture is tightly bound and essentially unavailable as indicated by the stability of aspirin in the presence of STARCH 1500.

The pregelatinized starch can be dried prior to mixing with cyclophosphamide. However, no significant differences have been observed using dried pregelatinized starches versus using undried pregelatinized starches.

Using STARCH 1500, it has been found that a cyclophosphamide/pregelatinized starch ratio of approximately 2:1 provides an adequate blend compatibility to produce core tablets that can be transferred intact for compression coating on a tablet press. Such a blend is advantageous because it is predominantly cyclophosphamide, resulting in a smaller, more easily swallowable tablet.

B. Additional Diluents

Optionally, other direct compression vehicles can be added to the core tablet blend. However, such diluents are not necessary because a core tablet blend of cyclophosphamide and pregelatinized starch is usually sufficiently compressible to provide an acceptable compressed core tablet. Moreover, the presence of other diluents might have a detrimental effect on stability. Other diluents include lactose monohydrate, microcrystalline cellulose, calcium phosphate (dibasic, milled), ungelatinized corn starch, and dextrates.

C. Disintegrants

Disintegrants are substances that are added to the ingredients of a pharmaceutical tablet to facilitate its disintegration in the presence of water or biological fluids, and thus hasten the release of the active ingredients. In experiments with the core tablet blend of this invention, sodium starch glycolate was used to facilitate disintegration. Experiments in which the level of disintegrant was 0.0 percent, 4.0 percent and 8.0 percent were carried out to evaluate the effects on tablet dissolution, disintegration, hardness, durability and weight variation. The test results indicated that increasing or decreasing the disintegrant level had no adverse effect on the physical attributes of the tablet. Even though the test results indicated that a disintegrant is unnecessary, it is preferred to include sodium starch glycolate at a 4.0 percent level to assure disintegration and performance of aged tablets or tablets made with different batches of excipients.

D. Lubricants

Lubricants are ingredients that can be added to a tablet blend to facilitate ejection of the tablets from the dies after compression and to prevent tablets from sticking to the punch faces. Acceptable tablets can be manufactured using magnesium stearate in concentrations of 0.25 percent, 0.5 percent and 1.0 percent of the tablet weight, with no tablet picking or sticking to the punch faces. However, a 1.0 percent concentration has a detrimental effect on tablet durability and maximum achievable hardness. Prolonged mixing of the powder blend containing 0.5 percent does not significantly effect the dissolution characteristics, durability or tablet compressibility, and therefore, approximately 0.5 percent magnesium stearate is a preferred level of lubricant.

E. Glidants

Glidants are compounds which are used to improve the flow of the powder blend and to minimize tablet weight variation. Core blends and the resulting tablets containing 0.0 percent, 0.2 percent and 0.5 percent colloidal silicon dioxide have been evaluated for flowability and weight variation. These results show that the addition of 0.2 percent and 0.5 percent improves core blend flowability and decreases tablet weight variation. The results also indicate that increasing the level of colloidal silicon dioxide beyond 0.2 percent does not further improve the flowability or weight variation. Therefore, 0.2 percent colloidal silicon dioxide is a preferred level of glidant in the core tablet blend.

It will be readily apparent to those skilled in the art that pregelatinized starches, diluents, disintegrants, lubricants and glidants other than those specifically recited can be used. Determining the optimum levels of such ingredients is well within the ordinary skill of such persons using routine experimentation similar to that described above.

II. THE PRESS COAT BLEND

As discussed above, cyclophosphamide is cytotoxic, and therefore direct contact with cyclophoshhamide is a potential health risk. Accordingly, after compressing the core tablet blend containing cyclophosphamide, a press coat blend of inert, edible materials is used to encapsulate the compressed core tablet blend.

It is preferable that the composition of the press coat blend contain pregelatinized starch, most preferably STARCH 1500. While pregelatinized starch is the only diluent required in the core tablet blend, tableting characteristics are poor when used as the only diluent in the press coat. For instance, tablet weight loss during durability testing was generally greater than 1.0 percent and tablet picking and sticking often occurred. Therefore, mixtures of pregelatinized starch and microcrystalline cellulose at concentrations of 3:1, 1:1 and 1:3 have been evaluated. When microcrystalline cellulose comprises at least 50 percent of the diluent, the resulting tablets have acceptable tableting characteristics. The stability of the cyclophosphamide is not influenced significantly by these ratios of pregelatinized starch to microcrystalline cellulose. Thus, it is preferred to use a press coat blend comprising one part pregelatinized starch and three parts microcrystalline cellulose.

The press coat blend can, of course, be comprised of other additives such as disintegrants, lubricants and glidants useful in preparing any direct compression tablets. The press coat can also include coloring additives to enable visual recognition of the tablet. In the case of CYTOXAN®, the press coat blend contains blue flecks which give the finished tablet a distinctive appearance. A discussion of how to color the tablets with blue flecks is given below.

III. PROCESSING THE TABLETS

A. Preparing the Core Tablet and Press Coat Blends

A schematic diagram of an overall process for preparing direct compression tablets in accordance with this invention is shown in FIG. 1.

The first step in preparing the core tablet blend is to deagglomerate the cyclophosphamide and additives such as sodium starch glycolate (disintegrant) and colloidal silicon dioxide (glidant) by dry screening in a rotary granulator. The deagglomeration step is used to break up aggregates of the cyclophosphamide and additives.

Experiments were carried out to determine whether a Model D. Fitzmill or a Colton Rotary Granulator could sufficiently deagglomerate cyclophosphamide, sodium starch glycolate and colloidal silicon dioxide. That was accomplished by passing the ingredients concurrently through the Fitzmill or Granulator. Laboratory experiments demonstrated that the Fitzmill equipped with a number 2A plate, knives forward and medium speed could sufficiently break apart aggregates of those excipients. That is, there were no visual lumps in the excipients after passing through the Fitzmill. Also, the Fitzmill and a rotary granulator equipped with a 12 mesh screen were both shown to be operable when large scale laboratory or production batches were prepared.

After deagglomeration, the mixture is dry blended together with the pregelatinized starch and other additives such as magnesium stearate (lubricant). A 2.5 cubic foot Peerless Radial Arm mixer can be used for the dry blending. Aliquots of core tablet blends have been taken from six different areas of the Peerless mixer and assayed for cyclophosphamide content. The results indicate that cyclophosphamide is adequately distributed throughout the core tablet blends after 2, 5 and 30 minutes of blending. Therefore, a blending time of five minutes is preferred. It is noted that blending for 30 minutes does not cause a slowing of the disintegration/dissolution rates of the resulting tablets.

To determine whether there is any significant variability among different mixers, both the core tablet and press coat blends were prepared in four different mixers, i.e., a 2.5 cubic foot Peerless Radial Arm mixer, a 5.0 cubic foot Patterson-Kelley Twin Shell blender, and a 3.3 cubic foot and a 22.2 cubic foot Lodige mixer.

Fifty-six batches of core tablet blends ranging in size from 2000 tablets to 138,000 tablets were blended. Content uniformity and dissolution test results revealed no significant variability among the four mixers. Core tablet blend and tablet assay results indicated that the potencies were near target and well within batch acceptance limits.

Compressibility test results of two scale-up batches indicate that prolonged blending has a slight effect on the coat blend compressibility. That is, the maximum mean hardness for the 100 mg tablets compressed from blends that were blended 2, 5 and 30 minutes were 34, 34 and 26 Strong-Cobb units (SCU), respectively. However, all of those maximum mean hardnesses were well above the intended upper limit of 18 SCU.

B. The Blue Fleck Granulation

Currently marketed CYTOXAN® tablets contain blue flecks in the coat to give the tablets a unique appearance. Using a wet granulation process, a blue fleck formulation was prepared containing lactose as the diluent, povidone as the granulating agent, and two aluminum lake colors, FD&C Blue #1 and FD&C Yellow #10. The ratio of five parts blue and one part yellow resulted in the desired color.

C. Tableting

Processes for tableting are well known to those skilled in the art. A Manestry D3A Dry Cota rotary tablet press has been used and provides good results. It will be appreciated by those skilled in the art that other tableting machines capable of compressing a tablet within a tablet can also be used.

Cracking along the tablet sidewall may be prevented by selecting tablet sizes with an adequate distance between the perimeter of the core tablet and the perimeter of the press coat. A distance of at least 0.0859 inch for the 100 mg product and 0.0625 inch (1/16") for the 25 mg and 50 mg products should be used.

Using various compression forces (0.1 to 6.0 tons), tablet hardness limits of 7.0 SCU to 11.0 SCU, 10.0 SCU to 14.0 SCU and 14.0 SCU to 18.0 SCU for the 25 mg, 50 mg and 100 mg tablets, respectively, will provide acceptable results. Those hardnesses result in acceptable adherence of the press coat to the core tablet for all three products, with no picking, capping or lamination. When the direct compression compositions are compressed within those hardness limits, no broken or chipped tablets have been found, and weight loss has been less than one percent. Tablet thicknesses are within five percent of the average thicknesses and tablet dissolution results are well within the specification of Q=75% in 45 minutes according to the U.S. Pharmacopeia National Formulary.

The invention is illustrated in the following examples. The examples do not limit the scope of the invention in any manner. All percentages and ratios are by weight unless otherwise stated.

Examples 1–3 illustrate the compositions and processes for producing batches of 100,000 direct compression tablets in accordance with this invention.

EXAMPLE 1

Composition of 25 mg DC Cyclophosphamide Tablets

| Ingredient | Quantity Per Tablet, mg |
|---|---|
| Core Tablet Blend: | |
| Crystalline Cyclophosphamide Monohydrate | 26.750 |
| Pregelatinized Starch, N.F. | 11.500 |
| Sodium Starch Glycolate | 1.500 |
| Magnesium Stearate | 0.200 |
| Colloidal Silicon Dioxide | 0.050 |
| Total | 40.000 |
| Press Coat Blend: | |
| Lactose Powder | 7.152 (1) |
| Color, FD&C Blue #1, Alum. Lake | 0.040 (1) |
| Color, D&C Yellow #10, Alum. Lake | 0.008 (1) |
| Povidone | 0.800 (1) |
| Microcrystalline Cellulose, N.F. | 79.800 |
| Pregelatinized Starch, N.F. | 27.000 |
| Sodium Starch Glycolate | 4.500 |
| Magnesium Stearate | 0.500 |
| Colloidal Silicon Dioxide | 0.200 |
| Total | 120.000 |
| Total (Whole Tablet) | 160.000 |

Note (1): Blue granulation.

Processing Instructions for 100,000 Tablets (25 mg)

Blue Granulation

1. Mix the following to dissolve:

| a. Povidone in | 40.0 g |
|---|---|
| b. Purified Water | 120.0 g |

2. Blend the following to achieve a rough blend:

| a. Lactose Powder | 200.0 g |
|---|---|
| b. Color, FD&C Blue #1 - Alum. Lake | 4.0 g |
| c. Color, D&C Yellow #10 - Alum. Lake | 0.8 g |

3. Mill or screen the rough blend to remove agglomerates and to facilitate dispersal of the colorants.
4. Blend the following until uniform in color:

| a. Milled or screened materials from Step 3. | |
|---|---|
| b. Povidone | 40.0 g |
| c. Lactose Powder | 515.2 g |

5. While blending, add the povidone solution to granulate the powders.
  Note: Additional water may be added if necessary to achieve the proper consistency.
6. Continue blending to achieve the desired consistency.
7. Dry the material until the moisture content is within specification limits.
8. Mill or screen the dried material to achieve a suitable particle side distribution.
9. Classify the sized material through a series of sieves to collect the fraction suitable for blue flecks (12 to 30 mesh).

Press Coat Blend

1. Blend the following to achieve a rough blend:

| | |
|---|---|
| a. Sodium Starch Glycolate | 450.0 g |
| b. Colloidal Silicon Dioxide | 20.0 g |

2. Mill or screen the rough blend to remove agglomerates.

3. Blend the following materials until homogenous:

| | |
|---|---|
| a. Milled or Screened Materials from Step 2. | |
| b. Pregelatinized Starch, N.F. | 2,700.0 g |
| c. Microcrystalline Cellulose, N.F. | 7,980.0 g |
| d. Magnesium Stearate | 50.0 g |
| e. Blue Granulation | 800.0 g |

Core Tablet Blend

1. Blend the following to achieve a rough blend:

| | |
|---|---|
| a. Cyclophosphamide Monohydrate | 2,675.0 g |
| b. Colloidal Silicon Dioxide | 5.0 g |

2. Mill or screen the rough blend to remove agglomerates.

3. Blend the following until homogenous:

| | |
|---|---|
| a. Milled or Screened Materials from Step 2. | |
| b. Pregelatinized Starch, N.F. | 1,150.0 g |
| c. Sodium Starch Glycolate | 150.0 g |
| d. Magnesium Stearate | 20.0 g |

Tablets

1. Compress the core tablet blend to provide core tablets ranging from 1.17 to 1.23 grams per 30 tablets with the minimum hardness that will allow transfer of the core tablets without breakage.

2. Compress the press coat blend around the transferred core tablet to provide whole tablet weights ranging from 1.57 to 1.63 grams per 10 tablets having hardness values ranging from 7 to 11 SCU.

EXAMPLE 2

Composition of 50 mg DC Cyclophosphamide Tablets

| Ingredient | Quantity Per Tablet, mg |
|---|---|
| Core Tablet Blend: | |
| Crystalline Cyclophosphamide Monohydrate | 53.50 |
| Pregelatinized Starch, N.F. | 23.00 |
| Sodium Starch Glycolate | 3.00 |
| Magnesium Stearate | 0.40 |
| Colloidal Silicon Dioxide | 0.10 |
| Total | 80.00 |
| Press Coat Blend: | |
| Lactose Powder | 8.94 (1) |
| Color, FD&C Blue #1, Alum. Lake | 0.05 (1) |
| Color, D&C Yellow #10, Alum. Lake | 0.01 (1) |
| Povidone | 1.00 (1) |
| Microcrystalline Cellulose, N.F. | 107.00 |
| Pregelatinized Starch, N.F. | 36.00 |
| Sodium Starch Glycolate | 6.00 |
| Magnesium Stearate | 0.70 |
| Colloidal Silicon Dioxide | 0.30 |
| Total | 160.00 |
| Total (Whole Tablet) | 240.00 |

Note (1): Blue granulation.

Processing Instructions for 100,000 Tablets (50 mg)

Blue Granulation

1. Mix the following to dissolve:

| | |
|---|---|
| a. Povidone in | 50.0 g |
| b. Purified Water | 150.0 g |

2. Blend the following to achieve a rough blend:

| | |
|---|---|
| a. Lactose Powder | 200.0 g |
| b. Color, FD&C Blue #1 - Alum. Lake | 5.0 g |
| c. Color, D&C Yellow #10 - Alum. Lake | 1.0 g |

3. Mill or screen the rough blend to remove agglomerates and to facilitate dispersal of the colorants.

4. Blend the following until uniform in color:

| | |
|---|---|
| a. Milled or screened materials from Step 3. | |
| b. Povidone | 50.0 g |
| c. Lactose Powder | 694.0 g |

5. While blending, add the povidone solution to granulate the powders.

Note: Additional water may be added if necessary to achieve the proper consistency.

6. Continue blending to achieve the desired consistency.

7. Dry the material until the moisture content is within specification limits.

8. Mill or screen the dried material to achieve a suitable particle side distribution.

9. Classify the sized material through a series of sieves to collect the fraction suitable for blue flecks (12 to 30 mesh).

Press Coat Blend

1. Blend the following to achieve a rough blend:

| | |
|---|---|
| a. Sodium Starch Glycolate | 600.0 g |
| b. Colloidal Silicon Dioxide | 30.0 g |

2. Mill or screen the rough blend to remove agglomerates.

3. Blend the following materials until homogenous:

| | | |
|---|---|---|
| a. | Milled or Screened Materials from Step 2. | |
| b. | Pregelatinized Starch, N.F. | 3,600.0 g |
| c. | Microcrystalline Cellulose, N.F. | 10,700.0 g |
| d. | Magnesium Stearate | 70.0 g |
| e. | Blue Granulation | 1,000.0 g |

Core Tablet Blend

1. Blend the following to achieve a rough blend:

| | | |
|---|---|---|
| a. | Cyclophosphamide Monohydrate | 5,350.0 g |
| b. | Colloidal Silicon Dioxide | 10.0 g |

2. Mill or screen the rough blend to remove agglomerates.
3. Blend the following until homogenous:

| | | |
|---|---|---|
| a. | Milled or Screened Materials from Step 2. | |
| b. | Pregelatinized Starch, N.F. | 2,300.0 g |
| c. | Sodium Starch Glycolate | 300.0 g |
| d. | Magnesium Stearate | 40.0 g |

Tablets

1. Compress the core tablet blend to provide core tablets ranging from 2.34 to 2.46 grams per 30 tablets with the minimum hardness that will allow transfer of the core tablets without breakage.
2. Compress the press coat blend around the transferred core tablet to provide whole tablet weights ranging from 2.35 to 2.45 grams per 10 tablets having hardness values ranging from 10 to 14 SCU.

EXAMPLE 3

Composition of 100 mg DC Cyclophosphamide Tablets

| Ingredient | Quantity Per Tablet, mg |
|---|---|
| Core Granulation: | |
| Crystalline Cyclophosphamide Monohydrate | 107.000 |
| Pregelatinized Starch, N.F. | 46.000 |
| Sodium Carboxy-Methyl Starch | 6.000 |
| Magnesium Stearate | 0.800 |
| Colloidal Silicon Dioxide | 0.200 |
| Total | 160.000 |
| Press Coat Granulation: | |
| Lactose Powder | 13.410[1] |
| Color, FD&C Blue #1, Alum. Lake | 0.075[1] |
| Color, D&C Yellow #10, Alum. Lake | 0.015[1] |
| Povidone | 1.500[1] |
| Microcrystalline Cellulose, N.F. | 160.500 |
| Pregelatinized Starch, N.F. | 54.000 |
| Sodium Carboxy-Methyl Starch | 9.000 |
| Magnesium Stearate | 1.050 |
| Colloidal Silicon Dioxide | 0.450 |
| Total | 240.000 |
| Total (Whole Tablet) | 400.000 |

Note
[1]Blue granulation.

Processing Instructions for 100,000 Tablets (100 mg)

Blue Granulation

1. Mix the following to dissolve:

| | | |
|---|---|---|
| a. | Povidone in | 75.0 g |
| b. | Purified Water | 225.0 g |

2. Blend the following to achieve a rough blend:

| | | |
|---|---|---|
| a. | Lactose Powder | 400.0 g |
| b. | Color, FD&C Blue #1 - Alum. Lake | 7.5 g |

| | | |
|---|---|---|
| c. | Color, D&C Yellow #10 - Alum. Lake | 1.5 g |

3. Mill or screen the rough blend to remove agglomerates and to facilitate dispersal of the colorants.
4. Blend the following until uniform in color:

| | | |
|---|---|---|
| a. | Milled or screened materials from Step 3. | |
| b. | Povidone | 75.0 g |
| c. | Lactose Powder | 941.0 g |

5. While blending, add the povidone solution to granulate the powders.
Note: Additional water may be added if necessary to achieve the proper consistency.
6. Continue blending to achieve the desired consistency.
7. Dry the material until the moisture content is within specification limits.
8. Mill or screen the dried material to achieve a suitable particle side distribution.
9. Classify the sized material through a series of sieves to collect the fraction suitable for blue flecks (12 to 30 mesh).

Press Coat Granulation

1. Blend the following to achieve a rough blend:

| | | |
|---|---|---|
| a. | Sodium Carboxy-Methyl Starch | 900.0 g |
| b. | Colloidal Silicon Dioxide | 45.0 g |

2. Mill or screen the rough blend to remove agglomerates.
3. Blend the following materials until homogenous:

| | | |
|---|---|---|
| a. | Milled or Screened Materials from Step 2. | |
| b. | Pregelatinized Starch, N.F. | 5,400.0 g |
| c. | Microcrystalline Cellulose, N.F. | 16,050.0 g |
| d. | Magnesium Stearate | 105.0 g |
| e. | Blue Granulation | 1,500.0 g |

Core Granulation

1. Blend the following to achieve a rough blend:

| | | |
|---|---|---|
| a. | Cyclophosphamide Monohydrate | 10,700.0 g |
| b. | Colloidal Silicon Dioxide | 20.0 g |

2. Mill or screen the rough blend to remove agglomerates.
3. Blend the following until homogenous:

| | | |
|---|---|---|
| a. | Milled or Screened Materials from Step 2. | |
| b. | Pregelatinized Starch, N.F. | 4,600.0 g |
| c. | Sodium Carboxy-Methyl Starch | 600.0 g |
| d. | Magnesium Stearate | 80.0 g |

Tablets

1. Compress the core tablet blend to provide core tablets ranging from 1.56 to 1.64 grams per 10 tablets with the minimum hardness that will allow transfer of the core tablets on the tablet press without breakage.

2. Compress the press coat blend around the transferred core tablet to provide whole tablet weights ranging from 3.92 to 4.00 grams per 10 tablets having hardness values ranging from 14 to 18 SCU.

Example 4 illustrates the unexpected stability achieved by direct compression tablets comprising cyclophosphamide and a pregelatinized starch.

EXAMPLE 4

The literature was reviewed to accumulate a list of available and commonly used direct compression excipients which could be used in a direct compression formulation for a 50 mg cyclophosphamide tablet. A preliminary screen of the following direct compression excipients was carried out.

1. FAST FLOW LACTOSE (lactose monohydrate)
2. AVICEL ® PH-101(microcrystalline cellulose)
3. STARCH 1500 (starch, pregelatinized)
4. Calcium phosphate dibasic (dihydrate, unmilled)
5. TABLETTOSE ® (lactose monohydrate)
6. EMDEX ® (dextrates)
7. Anhydrous Lactose D.T.

To test for compatibility, each excipient was blended with cyclophosphamide and compressed into discs containing one part cyclophosphamide and three parts excipient. Those discs were packaged in amber glass bottles and held at 30° C. and 40° C. The discs were examined periodically for discoloration only. The experimental discs were compared to two controls. One control was discs of the same composition held at 25° C. The second control was the core composition of currently marketed CYTOXAN ® tablets (CYTOXAN tablet core) compressed into discs and held at the same conditions a the experimental discs. The results of the first set of discs are shown in Tables I and II.

The direct compression discs were evaluated for physical stability with cyclophosphamide, which was judged by the change in appearance of the tablets. Historical data has suggested that discoloration of cyclophosphamide tablet cores indicates degradation. The appearance of the experimental discs were describe by the following four 1. No Change - The appearance was identical to the control in a side-by-side comparison with the control.

2. Slight Change - The change in appearance was slight and was not noticeable without comparison to a control.

3. Moderate Change - The change in appearance was moderate and noticeable without comparison to a control.

4. Significant Change - The change in appearance was severe in a side-by-side comparison with a control tablet.

A second set of discs was prepared similarly to the above except that the excipients were dried overnight in a forced air oven at 49° C. (120° F.) prior to blending with the cyclophosphamide. That was done to determine whether moisture content affected compatibility. The results of the second set of discs are shown in Tables III and IV. The moisture content of those excipients was determined by a Cenco Moisture Balance set at 100 volts for 10 minutes (Table V).

Results from the first two sets of discs (Tables I-IV) indicated that STARCH 1500 was the most compatible excipient with no change in appearance for at least 42 days at 40° C. However, it was found that when STARCH 1500 was used as the sole diluent, the blend could not be compressed to the desired hardness for normal pharmaceutical processing and handling. Therefore, a third series of discs was prepared in which the diluent was a better compressible combination of STARCH 1500 and other excipients. The combinations used were as follows:

1. STARCH 1500/AVICEL ®PH-101 (1:3)
2. STARCH 1500/dicalcium phosphate unmilled (1:3)
3. STARCH 1500/TABLETTOSE ® (1:3)
4. STARCH 1500/lactose, hydrous (1:3)

A diluent to cyclophosphamide ratio of 3:1 was used in the discs. Two additional controls were made for the third series of discs. One control had a diluent consisting only of lactose powder because that composition had not previously been studied. The diluent for the second control was comprised of lactose powder and corn starch in a ratio of 3:1. That control was added to compare the stabilizing effects of corn starch and STARCH 1500. The results of the third set of discs is shown in Table VI.

TABLE I

Change in Appearance of Compressed Discs Containing CY and D.C. Excipients Stored at 40° C.

| | 0 | 14 | 28 | 42 | 56 | 75 |
|---|---|---|---|---|---|---|
| CYTOXAN ® Tablet Core | ← | Slight Change | | → ← Mod Change → ← | Significant Change | → |
| STARCH 1500 | ← | No Change | | → ← | Slight Change | → |
| AVICEL ® PH-101 | ← Slight Change → ← | Mod Change → ← | Significant Change | | | → |
| Dicalcium Phosphate, unmilled | ← Mod Change → ← | Significant Change | | | | → |
| EMDEX ® (Dextrose) | ← Significant Change → ← | Discontinued | | | | → |
| FAST-FLOW Lactose | ← Significant Change → ← | Discontinued | | | | → |
| TABLETTOSE ® (Lactose) | ← Significant Change → ← | Discontinued | | | | → |
| Lactose Anhydrous | ← Significant Change → ← | Discontinued | | | | → |

TABLE II

Change in Appearance of Compressed Discs Containing CY and D.C. Excipients Stored at 30° C.

(Time, Days)

| | 0 | 14 | 28 | 42 | 56 | 75 |
|---|---|---|---|---|---|---|
| CYTOXAN ® Tablet Core | |————— No Change —————|———|———|※———| Slight Change →|
| STARCH 1500 | |————————————— No Change —————————————→|
| AVICEL ® PH-101 | |————————————— No Change —————————————→|
| Dicalcium Phosphate, unmilled | |————————————— No Change —————————————→|
| EMDEX ® (Dextrose) | No Change ← Mod Change ※ ———— Significant Change ————→ |
| FAST-FLO Lactose | No Change ← Mod Change ※ ———— Significant Change ————→ |
| TABLETTOSE ® (Lactose) | No Change ← Slight Change ※ ———— Moderate Change ————→ |
| Lactose Anhydrous | No Change ← Slight Change ※ ———— Moderate Change ————→ |

TABLE III

Change in Appearance of Compressed Discs Containing CY and Predried D.C. Excipients Stored at 40° C.

(Time, Days)

| | 0 | 14 | 28 | 42 | 56 | 75 |
|---|---|---|---|---|---|---|
| CYTOXAN ® Tablet Core | ←————— Slight Change —————※ Mod Change ※ Significant Change →|
| STARCH 1500 | ←————————————— No Change —————————————→|
| AVICEL ® PH-101 | ←Slight Change※— Mod Change —※——— Significant Change ———→|
| Dicalcium Phosphate, unmilled | ←Mod Change※———————— Significant Change ————————→|
| EMDEX ® (Dextrose) | ← Significant Change ※—————— Discontinued ——————→|
| FAST-FLO Lactose | ← Significant Change ※—————— Discontinued ——————→|
| TABLETTOSE ® (Lactose) | ← Significant Change ※—————— Discontinued ——————→|
| Lactose Anhydrous | ← Significant Change ※—————— Discontinued ——————→|

TABLE IV

Change in Appearance of Compressed Discs Containing CY and Predried D.C. Excipients Stored at 30° C.

(Time, Days)

| | 0 | 14 | 28 | 42 | 56 | 75 |
|---|---|---|---|---|---|---|
| CYTOXAN ® Tablet Core | ←————————— No Change —————————※——— slight Change →|
| STARCH 1500 | ←————————————— No Change —————————————→|
| AVICEL ® PH-101 | ←————————————— No Change —————————————→|
| Dicalcium Phosphate, unmilled | ←————————————— No Change —————————————→|
| EMDEX ® (Dextrose) | No Change | Mod Change ←——— Significant Change ———→|
| FAST-FLO Lactose | No Change ←————— Significant Change —————→|
| TABLETTOSE ® (Lactose) | |——— No Change ——※——— Moderate Change ———→|
| Lactose Anhydrous | |——— No Change ——※——— Moderate Change ———→|

TABLE V

The Percent Moisture Content of D.C. Excipients Before and After Drying at 120° F. for 18 Hours

| Excipient | Before Drying | After Drying |
|---|---|---|
| FAST FLO Lactose | 0.6 | 0.4* |
| AVICEL ® PH-101 | 4.2 | 2.2 |
| STARCH 1500 | 9.6 | 3.4 |
| TABLETTOSE ® (Lactose) | 0.2 | 0.5* |
| EMDEX ® (Dextrose) | 8.8 | 0.6 |
| Calcium Phosphate, Dibasic | 1.0 | 0.9* |
| Anhydrous Lactose, D.T. | 0.2 | 0.3* |

*Essentially no change - within experimental error of moisture balance.

TABLE VI

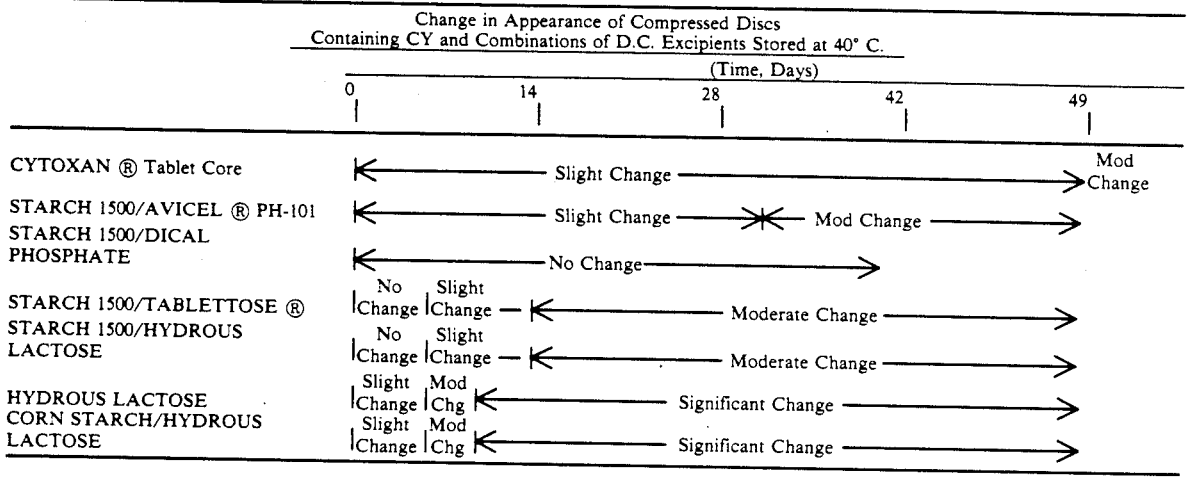

Results and Discussion

The changes in appearance of the first set of discs are illustrated in Tables I and II. It should be noted that the changes in appearance occurred gradually during the course of the study and not abruptly as the format of the tables might suggest. A review of Table I shows that the discs containing dextrose or lactose evidenced a significant change within one day when held at 40° C. The discs containing cyclophosphamide and AVICEL ® or dicalcium phosphate evidence a significant change in two to four weeks which was much earlier than the same change noted with the CYTOXAN ® tablet cores. The discs containing cyclophosphamide and STARCH 1500 showed very little change throughout the study and was far superior to the other excipients and the CYTOXAN ® tablet cores.

Table II shows the changes in appearance of the same set of discs held at 30° C. Here again, the discs containing cyclophosphamide and dextrose or lactose showed the most change in the least time. The CYTOXAN ® tablet cores showed only a slight change during the study. Discs containing cyclophosphamide and STARCH 1500, AVICEL ® or dicalcium phosphate did not change during the study.

Tables III and IV show the results for the second set of discs where the excipients were dried. AVICEL ®, STARCH 1500 and EMDEX ® were the only excipients that had a significant change in their moisture content after drying overnight (Table V). These results are essentially the same as those results for the first set of discs.

The results of the third series of discs are illustrated in Table VI. Table VI shows the additions of STARCH 1500 to AVICEL ®, TABLETTOSE ®, hydrous lactose or dicalcium phosphate definitely improved physical stability in comparison to these excipients alone (see Table I) when held at 40° C. Those combinations, however, were not as stable as discs containing cyclophosphamide and STARCH 1500 only as shown in Table I or CYTOXAN ® tablet cores with the exception that the cyclophosphamide and STARCH 1500/dicalcium phosphate discs were more stable than CYTOXAN ® tablet cores.

When results on the last three discs held at 40° C. containing cyclophosphamide and hydrous lactose are compared (Table VI), it is evident that STARCH 1500 had a stabilizing effect while corn starch did not. Corn starch and hydrous lactose comprise the diluent system of the currently marketed Cytoxan tablets.

In conclusion, the results indicated that pregelatinized starch (STARCH 1500) was the most physically compatible excipient within the limits of this study. Pregelatinized starch also appeared to improve the compatibility of other excipients with cyclophosphamide while corn starch did not. The moisture content of excipients did not affect compatibility.

EXAMPLE 5

Following the startling results of Example 4 in which the direct compression cyclophosphamide/pregelatinized starch composition showed unexpected stability, an experiment was performed to determine whether several brands of pregelatinized corn starches differ in their physical and/or chemical compatibility with cyclophosphamide. In the experiment, the following pregelatinized corn starches were substituted for the STARCH 1500 in the cyclophosphamide core blends. The source and type of each of the following pregelatinized starches has been previously described.

1. CERI-GEL 300
2. CERI-GEL 433
3. PREGEL
5. TENDER JEL
6. WHEATGEL 100
7. BINASOL ® 15
8. BINASOL ® 81
9. INSTANT TENDER JEL
10. STARCO 401
11. DURA-GEL ®
12. STAY-RX ®

Core blends for 2000 core tablets of each brand of corn starch were prepared in a Turbula (Model-T2A) mixer for five minutes. The blends were compressed into tablets on the Colton 216 rotary tablet press tooled with four stations of 7/32 inch tooling. The uncoated core tablets were packed in amber glass bottles and held at 30° C., 35° C. and 40° C. The results of the assays at 35° C. and 30° C. are shown in Tables VII and VIII. The results of the appearance tests at 40° C., 35° C. and 30° C. are shown in Tables IX, X and XI, respectively.

The characteristics of the tablets evaluated were appearance and chemical stability (potency). The appearance of the test tablets was compared to control tablets from the same batch held at room temperature. The appearance of the test tablets was described by the following four terms.

1. No Change - The test tablet was identical to the control in a side-by-side comparison with a control tablet.
2. Slight (sl) Change - The test tablet exhibited a slight change in a side-by-side comparison with a control tablet. The change was not noticeable without comparison to a control.
3. Moderate (mod) Change - The test tablet exhibited a moderate change in a side-by-side comparison with a control tablet. The change was noticeable without comparison to a control.
4. Significant (sig) Change - The test tablet exhibited a severe change in a side-by-side comparison with a control tablet.

TABLE VII

Assay Test Results For 50 mg D.C. Cyclophosphamide Core Tablets Containing Various Pregelatinized Starches Stored at 35° C.
(Percent of Target)

| Age (Weeks) | Ceri-Gel 300 | Ceri-Gel 443 | Pregel | Keogel 30 | Tender Jel 419 | Binasol 15 | Binasol 81 |
|---|---|---|---|---|---|---|---|
| 0 | 100.0, 99.6 | 100.2, 100.0 | 100.0, 99.2 | 101.8, 101.2 | 102.2, 101.0 | 101.6, 101.6 | 104.4, 101.0 |
| 10 | 97.6 | 90.2 | 98.4 | 99.2 | 99.2 | 98.4 | 98.2 |
| 26 | 89.8 | 92.6 | 95.8 | 85.2 | 94.6 | 92.8 | 88.6 |
| 39 | — | 76.6 | 92.4 | 84.2 | 90.0 | 85.0 | 83.2 |
| 52* | 36.2 | 59.2 | 61.0 | 48.6 | 37.0 | 35.6 | 42.6 |
| 78 | 30.8 | 28.0 | 43.6 | 35.8 | 25.2 | 31.6 | 31.4 |

| Age (Weeks) | Instant Tender Jel | Starco 401 | Dura-Gel | Sta-Rx | Wheatgel 100 | Starch 1500 |
|---|---|---|---|---|---|---|
| 0 | 102.2, 100.0 | 101.2, 102.0 | 101.8, 100.0 | 100.4, 101.8 | 103.4, 103.8 | 99.0, 102.0 |
| 10 | 98.8 | 98.8 | 98.8 | 100.2 | 91.8 | 97.4 |
| 26 | 98.6 | 100.2 | 100.4 | 98.0 | 101.2 | 98.2 |
| 39 | 99.2 | 101.4 | 98.4 | 98.2 | 101.6 | 97.4 |
| 52* | 77.8 | 41.6 | 43.4 | 95.2 | 53.6 | 64.6 |
| 78 | 37.4 | 44.4 | 35.0 | 41.2 | 40.6 | 43.6 |

*Assay was performed on a one tablet sample.

TABLE VIII

Assay Test Results For 50 mg D.C. Cyclophosphamide Core Tablets Containing Various Pregelatinized Starches Stored at 30° C.
(Percent of Target)

| Age (Weeks) | Ceri-Gel 300 | Ceri-Gel 443 | Pregel | Keogel 30 | Tender Jel 419 | Binasol 15 | Binasol 81 |
|---|---|---|---|---|---|---|---|
| 0 | 100.0, 99.6 | 100.2, 100.0 | 100.0, 99.2 | 101.8, 101.2 | 102.2, 101.0 | 101.6, 101.6 | 104.4, 101.0 |
| 26 | 100.8 | 101.0 | 100.2 | 102.4 | 102.4 | 103.8 | 99.2 |
| 39 | — | 98.6 | 100.6 | 99.8 | 101.4 | 99.6 | 100.0 |
| 78 | 94.8 | 95.0 | 96.0 | 98.6 | 101.8 | 102.6 | 101.4 |
| 104 | 97.8 | 95.6 | 97.8 | 100.8 | 98.0 | 99.4 | 98.8 |

| Age (Weeks) | Instant Tender Jel | Starco 401 | Dura-Gel | Sta-Rx | Wheatgel 100 | Starch 1500 |
|---|---|---|---|---|---|---|
| 0 | 102.2, 100.0 | 101.2, 102.0 | 101.8, 100.0 | 100.4, 101.8 | 103.4, 103.8 | 99.0, 102.0 |
| 26 | 98.6 | 100.2 | 100.4 | 98.0 | 101.2 | 98.2 |
| 39 | 99.2 | 101.4 | 98.4 | 98.2 | 101.6 | 97.4 |
| 78 | 101.0 | 99.0 | 99.0 | 100.2 | 99.6 | 94.6 |
| 104 | 98.6 | 99.0 | 99.6 | 92.0 | 99.8 | 91.8, 98.8 |

TABLE IX

Appearance Results for 50 mg D.C. Cyclophosphamide Core Tablets Containing Various Pregelatinized Starches Stored at 40° C.

| Age (Weeks) | Ceri-Gel 300 | Ceri-Gel 443 | Pregel | Keogel 30 | Tender Jel 419 | Binasol 15 | Binasol 81 |
|---|---|---|---|---|---|---|---|
| 0 | White | White | White | White | White | White | White |
| 4 | Sig Change | Sig Change | Sig Change | Sig Change | Sig Change | Sig Change | Sig Change |

| Age (Weeks) | Instant Tender Jel | Starco 401 | Dura-Gel | Sta-Rx | Wheatgel 100 | Starch 1500 |
|---|---|---|---|---|---|---|
| 0 | White | White | White | White | White | White |
| 4 | Sig Change | Sig Change | Sig Change | Sig Change | Sig Change | Sig Change |

TABLE X

Appearance Results for 50 mg D.C. Cyclophosphamide Core Tablets
Containing Various Pregelatinized Starches Stored at 35° C.

| Age (Weeks) | Ceri-Gel 300 | Ceri-Gel 443 | Pregel | Keogel 30 | Tender Jel 419 | Binasol 15 | Binasol 81 |
|---|---|---|---|---|---|---|---|
| 0 | White | White | White | White | White | White | White |
| 4 | No Change | No Change | No Change | No Change | No Change | No Change | No Change |
| 10 | No Change | No Change | No Change | No Change | No Change | No Change | No Change |
| 26 | No Change | No Change | No Change | No Change | No Change | No Change | No Change |
| 39 | Sl. Change | No Change | No Change | Sl. Change | No Change | Sl. Change | Sl. Change |
| 52 | Sl. Change | No Change | Sl. Change | Sl. Change | No Change | Sl. Change | Sl. Change |
| 78 | Sl. Change | Sl. Change | Sl. Change | Sl. Change | Sl. Change | Sl. Change | Sl. Change |

| Age (Weeks) | Instant Tender Jel | Starco 401 | Dura-Gel | Sta-Rx | Wheatgel 100 | Starch 1500 |
|---|---|---|---|---|---|---|
| 0 | White | White | White | White | White | White |
| 4 | No Change | No Change | No Change | No Change | No Change | No Change |
| 10 | No Change | No Change | No Change | No Change | No Change | No Change |
| 26 | No Change | No Change | No Change | No Change | No Change | No Change |
| 39 | No Change | No Change | No Change | No Change | No Change | No Change |
| 52 | Sl. Change | No Change | Sl. Change | No Change | Sl. Change | No Change |
| 78 | Sl. Change | Sl. Change | Sl. Change | Sl. Change | Sl. Change | Sl. Change |

TABLE XI

Appearance Results for 50 mg D.C. Cyclophosphamide Core Tablets
Containing Various Pregelatinized Starches Stored at 30° C.

| Age (Weeks) | Ceri-Gel 300 | Ceri-Gel 443 | Pregel | Keogel 30 | Tender Jel 419 | Binasol 15 | Binasol 81 |
|---|---|---|---|---|---|---|---|
| 0 | White | White | White | White | White | White | White |
| 4 | No Change | No Change | No Change | No Change | No Change | No Change | No Change |
| 10 | No Change | No Change | No Change | No Change | No Change | No Change | No Change |
| 26 | No Change | No Change | No Change | No Change | No Change | No Change | No Change |
| 39 | No Change | No Change | No Change | No Change | No Change | No Change | No Change |
| 52 | No Change | No Change | No Change | No Change | No Change | No Change | No Change |
| 78 | No Change | No Change | No Change | No Change | No Change | No Change | No Change |
| 104 | No Change | No Change | No Change | No Change | No Change | No Change | No Change |

| Age (Weeks) | Instant Tender Jel | Starco 401 | Dura-Gel | Sta-Rx | Wheatgel 100 | Starch 1500 |
|---|---|---|---|---|---|---|
| 0 | White | White | White | White | White | White |
| 4 | No Change | No Change | No Change | No Change | No Change | No Change |
| 10 | No Change | No Change | No Change | No Change | No Change | No Change |
| 26 | No Change | No Change | No Change | No Change | No Change | No Change |
| 39 | No Change | No Change | No Change | No Change | No Change | No Change |
| 52 | No Change | No Change | No Change | No Change | No Change | No Change |
| 78 | No Change | No Change | No Change | No Change | No Change | No Change |
| 104 | No Change | No Change | No Change | No Change | No Change | No Change |

Results and Discussion

Tables VII and VIII contain the assay results of the test core tablets held at 35° C. and 30° C., respectively. The core tablets were not assayed if they were physically unstable, i.e., severely discolored or liquified, which is why none of the core tablets held at 40° C. were assayed.

The 35° C. assay results (Table VII) indicated that the cyclophosphamide within all 13 test core tablets degraded. However, the degradation rate of the cyclophosphamide varied with the various batches. INSTANT TENDER JEL, STARCO 401, DURA-GEL®, STA-RX®, WHEATGEL 100 and STARCH core tablets were physically stable and within two percent of their zero-hour results after 26 weeks. CERI-GEL 300, KOEGEL 30 and BINASOL 81 core tablets were the only tablets that assayed below 90 percent of the target after 26 weeks. Twelve of the 13 test batches assayed at less than percent of their zero-hour values after 52 weeks. STA-RX® core tablets assayed at 95.2 percent after 52 weeks. However, even those core tablets indicated significant degradation of the cyclophosphamide after 78 weeks.

All the core tablets were near their zero-hour results after 78 weeks of 30° C. (Table VIII). Eleven of the test batches assayed within 3.0 percent of their zero-hour results after 104 weeks of storage. CERI-GEL 433 and STA-RX® core tablets were 95.6 percent and 92.0 percent, respectively, of their zero-hour results.

Tables IX, X and XI contain the appearance results of the core tablets held at 40° C., 35° C. and 30° C., respectively. At 40° C., the cyclophosphamide in 12 of the 13 test batches evidenced significant changes after four weeks of storage. STARCH 1500 core tablets showed a slight change from their zero-hour appearance.

At 35° C., eight of the 13 test batches evidenced a slight change, a yellowing of the tablets, after 52 weeks of storage. CERI-GEL 443, TENDER JEL 419, STARCO 401, STA-RX® and STARCH 1500 did not evidence this change in appearance until 78 weeks of storage.

At 30° C., the 13 test batches did not evidence any changes from their zero-hour appearance during the 104 weeks of this study.

In conclusion, the results indicated that the various pregelatinized corn starches had essentially the same physical compatibility with cyclophosphamide at accelerated age conditions. All the core tablets evidenced a significant degradation of cyclophosphamide at 35° C. However, the time required for the tablets to assay less than 90 percent of target varied among the various brands of corn starch. There was no significant degradation of the cyclophosphamide among the core tablets, however, when they were held for 104 weeks at 30° C.

EXAMPLE 6

An experiment similar to that shown above in Example 4 was performed for 50 mg direct compression cyclophosphamide core tablets containing various direct compression diluents prepared in accordance with Example 2. This provides tablet cores comprising a ratio of cyclophosphamide to diluent of 2:1 by weight. The results of the testing are shown in Tables XII, XIII, XIV and XV and are somewhat redundant of the results shown in Example 4, with exception that this experiment provides both potency test results and direct physical comparison at several temperatures of the stabilizing effect of pregelatinized starch (STARCH 1500) and ungelatinized corn starch. Additionally, comparisons are made with other commonly used excipients. The terms for the appearance of the experimental tablets, i.e., no change, slight change, moderate change and significant change, are the same as described above in Examples 4 and 5.

TABLE XII

Appearance Results for 50 mg D.C. Cyclophosphamide Core Tablets Containing Various D.C. Diluents When Stored at 40° C.

| Age (Weeks) | Spray Dried Lactose | Starch 1500 | Avicel ® | Calcium Phosphate | Emdex ® | Corn Starch | Mannitol |
|---|---|---|---|---|---|---|---|
| 0 | White | White | White | White | White | White | White |
| 4 | Sig. Change | No Change | Mod. Change | Sig. Change | Sig. Change | Sig. Change | Sig. Change |
| 8 | * | Sig. Change | Sig. Change | * | * | * | * |
| 8 | | * | * | | | | |

*Core tablets were terminated after the indicated weeks of storage.

TABLE XIII

Appearance Results for 50 mg D.C. Cyclophosphamide Core Tablets Containing Various D.C. Diluents When Stored at 35° C.

| Age (Weeks) | Spray Dried Lactose | Starch 1500 | Avicel ® | Calcium Phosphate | Emdex ® | Corn Starch | Mannitol |
|---|---|---|---|---|---|---|---|
| 0 | White | White | White | White | White | White | White |
| 4 | Mod. Change | No Change | No Change | No Change | Sig. Change | Mod. Change | Mod. Change |
| 12 | Sig. Change | No Change | No Change | No Change | * | Mod. Change | Mod. Change |
| 20 | * | Sl. Change | Sl. Change | Sl. Change | | Mod. Change | Mod. Change |
| 30 | | Sl. Change | Sl. Change | Sl. Change | | Sig. Change | Mod. Change |
| 34 | | Sl. Change | Sl. Change | * | | * | * |
| 39 | | Sl. Change | Mod. Change | | | | |
| 52 | | Sl. Change | * | | | | |
| 52 | | * | | | | | |

*Core tablets were terminated after the indicated weeks of storage.

TABLE XIV

Appearance Results for 50 mg D.C. Cyclophosphamide Core Tablets Containing Various D.C. Diluents When Stored at 30° C.

| Age (Weeks) | Spray Dried Lactose | Starch 1500 | Avicel ® | Calcium Phosphate | Emdex ® | Corn Starch | Mannitol |
|---|---|---|---|---|---|---|---|
| 0 | White | White | White | White | White | White | White |
| 4 | No Change | No Change | No Change | No Change | Mod. Change | No Change | No Change |
| 8 | Mod. Change | No Change | No Change | No Change | Mod. Change | No Change | No Change |
| 12 | Mod. Change | No Change | No Change | No Change | Sig. Change | No Change | No Change |
| 16 | Mod. Change | No Change | No Change | No Change | Sig. Change | Mod. Change | Mod. Change |
| 39 | * | No Change | No Change | No Change | * | * | * |
| 52 | | No Change | No Change | No Change | | | |
| 52 | | * | * | * | | | |

*Core tablets were terminated after the indicated weeks of storage.

TABLE XV

Assay Test Results for 50 mg Cyclophosphamide Core Tablets Containing Various D.C. Diluents When Stored at 30° C. and 35° C. (Percent of Target)

| Storage Condition | Age (Weeks) | Spray Dried Lactose | Starch 1500 | Avicel ® | Calcium Phosphate | Emdex ® | Corn Starch | Mannitol |
|---|---|---|---|---|---|---|---|---|
| | 0 | 98.6, 99.6 | 114.8, 116.2 | 116.2, 116.4 | 113.8, 116.6 | 116.6. | 113.8. | 113.6. |
| 35° C. | 12 | 93.4 | 115.4 | 116.2 | 107.8 | 118.8 | 115.4 | 114.2 |
| | 26 | a | 109.4 | 102.2 | 68.2 | a | 108.6 | 107.2 |
| | 39 | — | 100.4 | 78.0 | — | — | 95.0 | 78.0 |
| | 52 | — | 91.6 | — | — | — | a | a |
| 30° C. | 39 | 97.4 | — | — | — | 114.8 | 112.4 | 109.4 |

TABLE XV-continued

Assay Test Results for 50 mg Cyclophosphamide Core Tablets
Containing Various D.C. Diluents When Stored at 30° C. and 35° C.
(Percent of Target)

| Storage Condition | Age (Weeks) | Spray Dried Lactose | Starch 1500 | Avicel ® | Calcium Phosphate | Emdex ® | Corn Starch | Mannitol |
|---|---|---|---|---|---|---|---|---|
| | 52 | a | 116.2 | 116.0 | 112.8 | a | a | a | a The core tablet was physically unstable; therefore, assays were not performed.

Results and Discussion

The results shown in Tables XII, XIII, XIV and XV clearly indicate that the pregelatinized starch (STARCH 1500) provides an unexpected and remarkable stabilizing effect on cyclophosphamide at age accelerating conditions of 40° C., 35° C. and 30° C. when compared with ungelatinized corn starch. This was also true of the other excipients tested.

While several advantageous embodiments have been chosen to illustrate the invention, it will be understood by those skilled in the art that various changes and modifications can be made therein without departing from the scope of the invention as defined in the appended claims.

What is claimed is:

1. A directly compressible pharmaceutical composition comprising cyclophosphamide and a partially or fully pregelatinized starch.

2. A pharmaceutical composition according to claim 1 wherein said pregelatinized starch is a partially pregelatinized corn starch comprising 15 percent by weight of free amylopectin, 5 percent by weight free amylose and 80 percent by weight unmodified corn starch.

3. A pharmaceutical composition according to claim 1 wherein said partially pregelatinized starch is a partially pregelatinized corn starch having a cold water soluble fraction of 10-20 percent.

4. A pharmaceutical composition according to claim 2, wherein the ratio of cyclophosphamide to partially pregelatinized starch in said composition is about 2 to 1 by weight.

5. A pharmaceutical composition according to claim 3, wherein the ratio of cyclophosphamide to partially pregelatinized starch in said composition is about 2 to 1 by weight.

6. A pharmaceutical composition according to claim 1, wherein the pregelatinized starch is a fully pregelatinized starch.

7. A pharmaceutical composition according to claim 6, wherein the ratio of cyclophosphamide to fully pregelatinized starch in said composition is about 2 to 1 by weight.

8. A tablet obtained by compressing the composition of claim 2.

9. A tablet obtained by compressing the composition of claim 3.

10. A tablet obtained by compressing the composition of claim 4.

11. A tablet obtained by compressing the composition of claim 5.

12. A tablet obtained by compressing the composition of claim 6.

13. A tablet obtained by compressing the composition of claim 7.

14. A direct compressible tablet comprising an inner core of compressed cyclophosphamide and partially or fully gelatinized starch, said core being coated with an inert edible coating.

* * * * *

UNITED STATES PATENT AND TRADEMARK OFFICE
CERTIFICATE OF CORRECTION

PATENT NO. : 5,047,246

DATED : September 10, 1991

INVENTOR(S) : Gallian, et al.

It is certified that error appears in the above—identified patent and that said Letters Patent is hereby corrected as shown below:

Claim 1, column 25, line 26, before the word "A" insert the words -- A tablet comprising --.

Claim 1, column 25, line 28, after the word "starch" insert the words -- wherein the ratio of cyclophosphamide to partially or fully pregelatinized starch in said composition is about 2 to 1 by weight --.

Claim 14, column 26, line 35, before the word "A" insert the words -- A tablet comprising --.

Claim 14, column 26, line 37, after the word "starch" insert the words -- wherein the ratio of cyclophosphamide to partially or fully pregelatinized starch in said tablet is about 2 to 1 by weight --.

Signed and Sealed this

Seventh Day of September, 1993

Attest:

BRUCE LEHMAN

*Attesting Officer*     *Commissioner of Patents and Trademarks*